United States Patent [19]

Effert

[11] Patent Number: 4,729,652

[45] Date of Patent: Mar. 8, 1988

[54] APPARATUS AND METHOD FOR DETERMINING ANGULAR ORIENTATION OF EYE

[75] Inventor: Rolf Effert, Aachen, Fed. Rep. of Germany

[73] Assignee: Eye Research Institute of Retina Foundation, Boston, Mass.

[21] Appl. No.: 794,752

[22] Filed: Nov. 4, 1985

[51] Int. Cl.⁴ .............................................. A61B 3/14
[52] U.S. Cl. ..................................... 351/210; 351/245
[58] Field of Search ................ 351/206, 209, 210, 245

[56] References Cited

U.S. PATENT DOCUMENTS

| | | | |
|---|---|---|---|
| 3,462,604 | 8/1969 | Mason | 351/210 |
| 3,598,107 | 8/1971 | Ishikawa et al. | 351/210 |
| 3,724,932 | 4/1973 | Cornsweet et al. | 351/210 |
| 3,804,496 | 4/1974 | Crane et al. | 351/210 |
| 4,019,813 | 4/1977 | Cornsweet et al. | 351/210 |
| 4,075,657 | 2/1978 | Weinblatt | 358/93 |
| 4,256,384 | 3/1981 | Kani et al. | 351/211 |
| 4,257,688 | 3/1981 | Matsumura | 351/210 |
| 4,287,410 | 9/1981 | Crane et al. | 351/210 |
| 4,370,033 | 1/1983 | Kani et al. | 351/211 |
| 4,373,787 | 2/1983 | Crane et al. | 351/210 |
| 4,528,989 | 7/1985 | Weinblatt | 128/745 |

OTHER PUBLICATIONS

A New Method of Determining Squint Angle in Primary and All Secondary Positions Using First and Fourth Purkinje Images, Effert.
Accurate Two Dimensional Eye Tracker Using First and Fourth Purkinje Images; Cornsweet et al., 8-1973, Optical Society of Am., pp. 921-928.

*Primary Examiner*—John K. Corbin
*Assistant Examiner*—P. M. Dzierzynski
*Attorney, Agent, or Firm*—Lahive & Cockfield

[57] ABSTRACT

An apparatus for performing measurements on the eye of a subject includes a headrest for supporting the head of the subject in a fixed position, and a frame holding a light source directing illumination at the eye. The frame is adapted for pivotal motion about a central axis of the eye. Imaging means provides an image of the first and fourth Purkinje images of the light, and means are provided for measuring the amount of rotation of the frame. The frame may be initially aligned so that a fixation target lies in the plane defined by the central axis and the light source, and then rotated until the first and fourth Purkinje images determine a straight line parallel to the central axis, whereby the plane is aligned with the optical axis of the eye. The net rotation of the frame then gives a direct reading of the angular difference between the line to the target and the optical axis of the eye. Preferably the apparatus includes an infrared light source. The apparatus may further include a filter to selectively pass infrared light, the filter being movable into a position to block the vision of the eye. Methods of using the invention to detect squint angles and latent squint angles are disclosed.

14 Claims, 10 Drawing Figures

APPARATUS AND METHOD FOR DETERMINING ANGULAR ORIENTATION OF EYE

FIELD OF THE INVENTION

This invention relates in general to optometric apparatus and methods. More particularly, it relates to an instrument and method for determining the angle between a visual axis and the optical axis of the eye, and for determining squint angles.

BACKGROUND OF THE INVENTION

Numerous ocular conditions are known which result in the two eyes of an individual actually aiming at different points in space when the individual attempts to fixate on a target. Strabismus, or wall-eye, for instance, may be caused by various factors, including a relative weakness of one eye muscle, or the anomalous attachment or dimension of an eye movement muscle. As a diagnostic indicator of such underlying conditions, it is useful to measure the angle of deviation of the affected eye. This deviation is usually expressed in terms of its horizontal and vertical components, termed the horizontal (respectively, vertical) squint angle.

One conventional method of ascertaining that the squint angle is not zero, which is the desired normal condition, is to have the subject fixate at a distant target and then, while closely observing an eye of the subject, cover the other eye. If the uncovered eye jumps to a new position, it was previously aimed at a position offset from the target. This cover test method requires the diagnostician to observe closely the eye during a fraction of a second; the test determines the existence of a squint angle, but not its amount. A cover test using also a graded sequence of prisms may be used to quantify the deviation. A clinical method for quantifying an amount of angular deviation is the use of an amblyoscope, in which each eye separately visualizes an image, the image presented to one eye being offset via an optical path of adjustable angle from the image presented to the other eye. The optical path is adjusted until the two images coincide, with the horizontal offset of the path providing a measure of the relative angular displacement of the two eyes.

Another, non-quantified, technique for determining the existence of a squint angle has been practiced by J. Lang, reported in Mikrostrabismus. Vol. 62, Bucherei des Augenarztes, 2nd ed., Stuttgart: Enke Verlag, 1982. In this technique, the eyes of the subject are illuminated from above with a photoflash as a frontal photograph is made of the two eyes, so as to show the first and fourth Purkinje images, which are seen as a pair of small spaced-apart dots visible through the pupil. One eye is then covered and a second photograph taken. If the Purkinje images of the second photograph have changed position, this indicates that the eye has readjusted its aim after covering of the first eye. The method of Lang essentially derives from the work of M. Tscherning in the 19th century, who observed the first and fourth Purkinje images from directly in front of an eye illuminated from above. Tscherning used such observations, reported in his Optique Physiologique, Paris 1898, to determine the difference between the optical axis and the fixation line of the eye.

More recently, numerous researchers have utilized images of the first and fourth Purkinje images as a non-invasive means of tracking movement of the eye itself. Among such efforts are the devices shown in U.S. Pat. Nos. 3,712,716; 3,724,932; and 3,804,496 all issued for inventions of Tom N. Cornsweet and Hewitt B. Crane. Those patents show generally an instrument for imaging the first and pair of split-field intensity discriminating photo cells to control a tracking mirror, so as to develop signals indicative of the actual eye movement. Related devices are shown in U.S. Pat. Nos. 4,287,410 and 4,373,787, both issued to Hewitt D. Crane and Carroll M. Steele.

It is also known in the art to utilize a light source and a video camera to image the human eye for measuring or other clinical purposes, as in U.S. Pat. Nos. 3,598,107 of Ishikawa et al.; 4,257,688 of Matsumura; and 4,370,033 of Kani et al.

BRIEF DESCRIPTION OF THE INVENTION

It is an object of the invention to provide a clinical instrument and method to determine a variety of occular measurements.

It is another object of the invention to provide a clinical instrument and method for directly determining squint angles of a subject in different gaze positions.

It is another object of the invention to provide a clinical instrument and method for determining squint angles with near and far fixation targets.

It is another object of the invention to provide a clinical instrument and method to provide a direct reading of the optical orientation of the eye.

It is another object of the invention to provide a clinical instrument and method admitting simple calibration, alignment and reading.

These and other features of the invention are obtained by providing an apparatus which may be aligned with a fixation target for performing measurements on the eye of a subject. A headrest supports the head of the subject in a fixed position, and a frame holds a light source directing illumination at the eye. The frame is aligned for pivotal motion about a central axis of an eye of the subject. Imaging means provides an image of the first and fourth Purkinje images of the light. The frame is initially aligned so that the fixation target lies in the plane defined by the central axis and the light source. The frame is then rotated until the first and fourth Purkinje images determine a straight line parallel to the central axis. At this position, the plane is aligned with the optical axis of the eye. Means are provided for measuring the amount of rotation of the frame, which gives a direct reading of the angular difference between the line to the target and the optical axis of the eye. By performing the reading separately on each eye, with the subject fixating, the difference in angular readings gives the squint angle. When the central eye axis about which the frame rotates is chosen to be the vertical axis of the eye, the angular reading is the horizontal squint angle; when the central eye axis is selected to be the horizontal axis of the eye, the angular reading is the vertical squint angle. Methods according to the invention enable one to determine the orientation of the optical axis, to determine squint angles, and to determine latent squint angles.

BRIEF DESCRIPTION OF THE DRAWINGS

These and other features of the invention will be more clearly understood by reference to the drawings, in which.

DETAILED DESCRIPTION OF ILLUSTRATED EMBODIMENT

The invention is best understood after a brief description of its theory of operation. Once the theory is known, it will be appreciated that the invention itself provides an apparatus and method according to which a diagnostician, by rotating a light source and aligning an easily perceived pattern of dot-like images in the eye, can quickly measure various eye angles of importance.

When a collimated light beam falls on the eye, each of four surfaces (front and back of the cornea and front and back of the lens) forms an image due to its partial reflection of the light source. These images are the so-called Purkinje images and are numbered sequentially according to the reflective surface forming them. The first, second and third images are virtual and erect because they are formed by reflection from a convex mirror-like surface. The fourth image, formed by reflection of the concave rear inner surface of the lens, is real and inverted. The first Purkinje image is the brightest, and is located in approximately the same plane as the fourth Purkinje image. The fourth image has a brightness of approximately one-hundredth times that of the first image. The luminosities of both images are such that they can be imaged with a video camera under appropriate circumstances.

According to the present invention, the relative position of the first and fourth Purkinje images are utilized to determine the orientation of the optical axis with respect to the incidence angle of a light source, or to develop a reading of the angular displacement of a visual axis or of the fixation axis of the eye from its optical axis.

Figure 1:
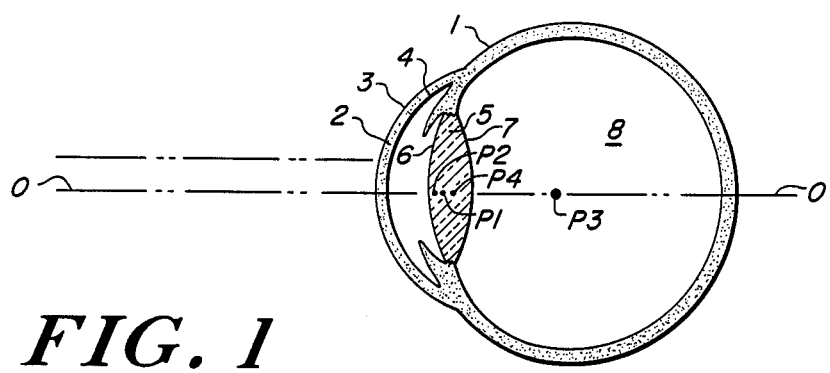
FIG. 1 is a schematic view of the eye and Purkinje images.

FIG. 1 shows a schematic view of the Purkinje image in the eye formed by incident light parallel to the optical axis 0 of the eye. As shown, the eye 1 includes the cornea 2 having front surface 3 and back surface 4 and also includes a lens 5 located within the vitreous humor 8 and having front surface 6 and back surface 7. Eye 1 is shown in cross-section, with the optical axis 0 passing centrally through the cornea and lens.

Figure 1A:
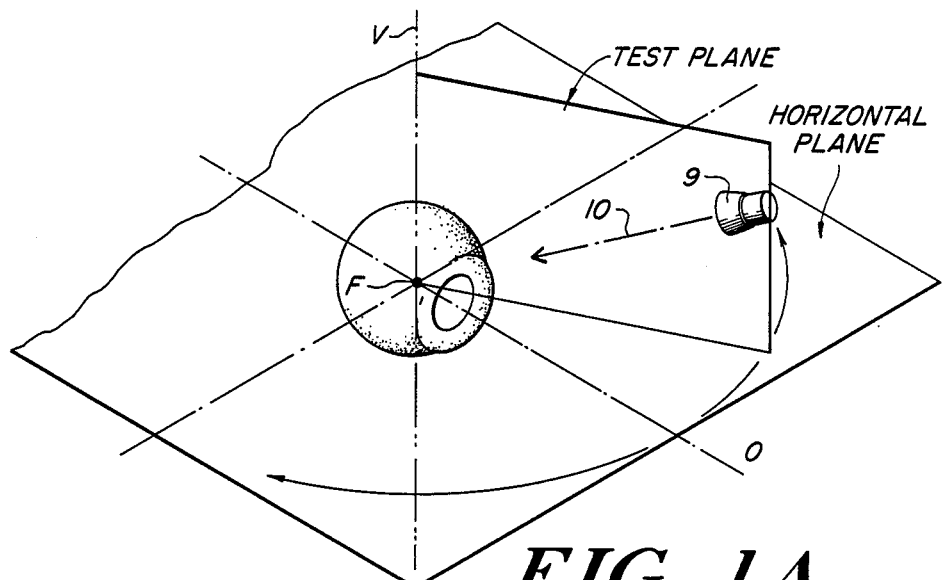
FIG. 1A shows a view of the eyeball and its axes aligned in relation to components of the invention in a flat orientation.

FIG. 1A shows a schematic view of the position of the light source of the present invention in relation to the eye. With illumination parallel to the optical axis, the Purkinje images P1, P2, P3, P4 all lie on the optical axis. The images P1 and P4 are approximately coincident. The eye is moved by muscles attached around its circumference, to rotate vertically, and rotate horizontally. Such rotations result in one central point F of the eye remaining fixed. Horizontal rotations of the eye rotate around a vertical axis V which passes centrally through the eye. Light source 9 is aimed to direct a collimated beam 10 at the cornea 2. The central vertical axis V and the light source 9 (or beam 10) determine a plane, referred to herein as the test plane.

When the eye is illuminated from a point in the test plane lying above the optical axis, the first Purkinje image will lie above the axis and the fourth Purkinje image will lie below the axis. Furthermore, as the test plane rotates about the vertical axis V of the eye, the first Purkinje image shifts laterally in the direction of the rotation, and the fourth image shifts laterally in the opposite direction.

The present invention employs these physical properties to provide a frame holding a light source directed at the eye and movable about the central axis of the eye. Imaging means displays an image of the first and fourth Purkinje images of the light. These two point-like images determine a line, and the direction of the line is a function of the angular displacement of the test plane from the optical axis. By initially aligning the test plane with a target, and then moving the test plane until the Purkinje images lie on a line parallel to the central axis, the rotation of the test plane provides a direct reading of the angular displacement of the optical axis of the eye from the target.

Figure 1B:
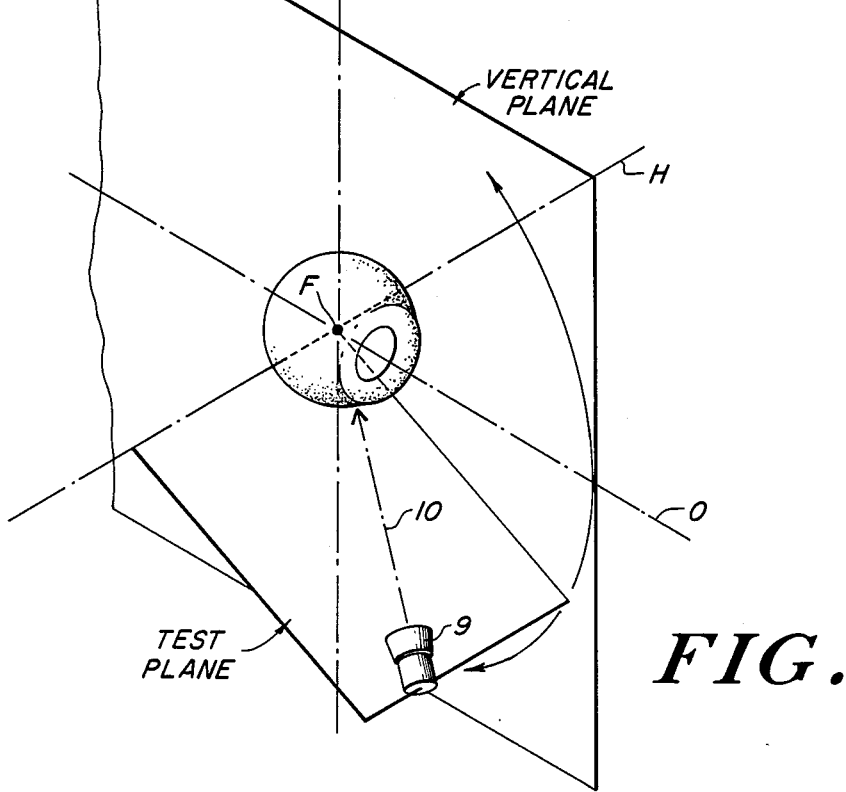
FIG. 1B shows another view of the eyeball and its axes in relation to components of the invention in another orientation.

FIG. 1B shows a schematic view of the eye in relation to an alternative orientation of the elements of the invention. The eye 1 has a horizontal central axis H and is illuminated by a light source 9 directed at the cornea 2 from one side of the eye. The light source 9 and axis H define a test plane movable about the horizontal axis. When illuminated from the side with a light source rotatable about the horizontal axis H, the first and fourth Purkinje images will determine a horizontal line only if the test plane coincides with the optical axis. The invention employs this relationship to directly measure the angular orientation of the optical axis in a vertical plane.

Figure 2:
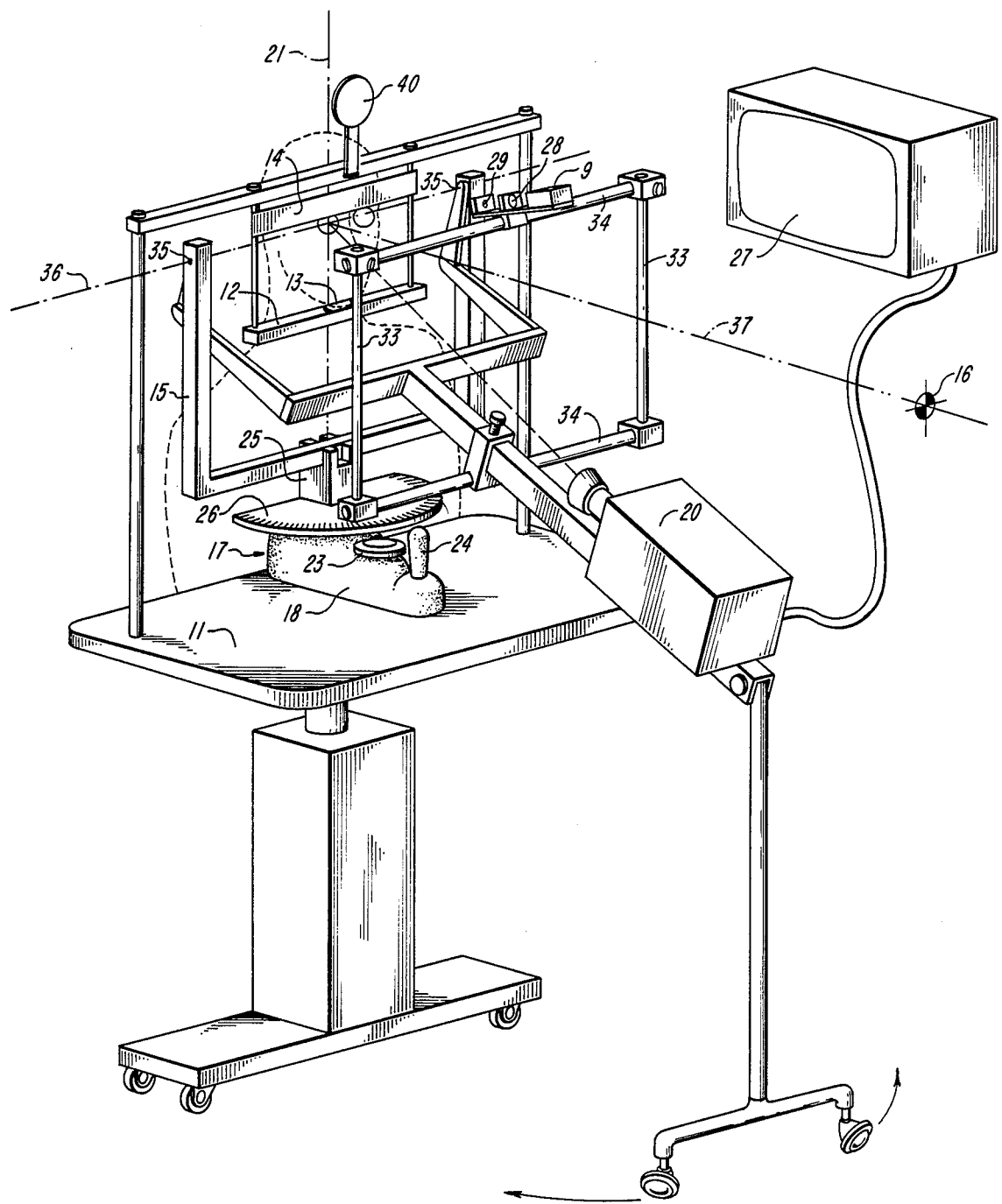
FIG. 2 is a schematic perspective view of an embodiment of the invention with fixation target.

FIG. 2 shows a perspective view of a clinical apparatus according to one embodiment of the invention. A platform 11 holds a head rest 12 comprising a chin rest 13 and a forehead band 14 configured to support the head of a subject 15 in a relaxed and stationary position. A filter 40 is provided adjacent the head rest, for use in a method of detecting phorie, discussed below. The platform and head rest are aligned with a distant target 16, which is centered between the eyes of the subject at approximately eye level six meters in front of the subject. Resting on platform 11 is a movable structure 17 having a positioning member 18 and a frame 19. The illustrated positioning member 18 is a rollable base portion, movable on the platform to permit alignment of the frame 19 with respect to the eye of the subject. A positioning handle 24 aids manipulation. In addition, the positioning member 18 has a vertical adjustment knob 23 operative, in a manner known in the art, to provide raising or lowering motion of a vertical positioning portion 25 of the frame 19. Frame 19 extends around the eyes of the subject, and includes an adjustable holding means 33, 34 holding a light source 9, and also holding an imaging means, shown as a video camera 20, aimed at the eye.

The frame 19 is adapted to pivot around the vertical axis shown at 21, and, in use, the positioning member 18 is moved to align the axis to coincide with the vertical axis of the subject's eye (V of FIG. 1). The vertical adjustment knob 23 is then turned to raise or lower the frame so that the light source 9, which is aimed at the pivot axis 21 will be aimed specifically at the cornea of the subject's eye. A graduated angular rotation scale 26 is affixed to the base, and a pointer member attached to the frame indicates the amount of angular rotation about the vertical axis of the frame unit. Video camera 20 is connected to a monitor 27 so as to display an image of the eye. In the illustrated embodiment, light source 9 is a P-N gallium arsenide infrared light emitting diode, TIL 31B supplied by Texas Instruments. The diode has a power consumption in the range of 5 milliwatts, and is positioned at the focal point of a positive lens 28 so as to provide a collimated beam. An iris stop 29 is placed in optical alignment with the source between the lens and the pupil to provide a beam of collimated light of a width approximating the corneal diameter. The video camera 20 is a high-sensitivity infrared black and white TV camera. One suitable camera is an MTI-DAGE 65 series camera with an Ultracon improved silicon target vidicon tube, RCA 4532-U.

In the configuration shown, the light source is aimed vertically downward and the camera is placed under the light source and observes the eye from below. The camera and light mount on the same holder and preferably in the same vertical plane so as to eliminate parallax effects. The exact angle at which the light source is directed downwardly is a matter of choice and will be determined to some extent by factors such as the size of the subject's eye. Slide clamps 32 and rods 33, 34 of the holding means provide for adjustment to vary the incident angle of the beam on the eye, so as to provide sufficient separation of the Purkinje images (approximately 3 mm) without causing the fourth Purkinje image to disappear behind the iris.

A brief discussion of the Purkinje images will clarify the purpose of the adjustable light holder. As shown in FIG. 1, the first, second, third and fourth Purkinje images (denoted P1, P2, P3 and P4 respectively) are formed, in response to the incident beam parallel to the optical axis, in spaced-apart positions along the optical axis so that all four images are substantially occluded by the image of P1, which is significantly brighter and larger than the others. The first and fourth images (P1, P4) are approximately coincident in a small region within the eye approximately in the location of lens 5. The holder 32, 33, 34 is devised to cause the images P1, P4 to be formed with sufficient density and separation to be imaged.

Figure 3:
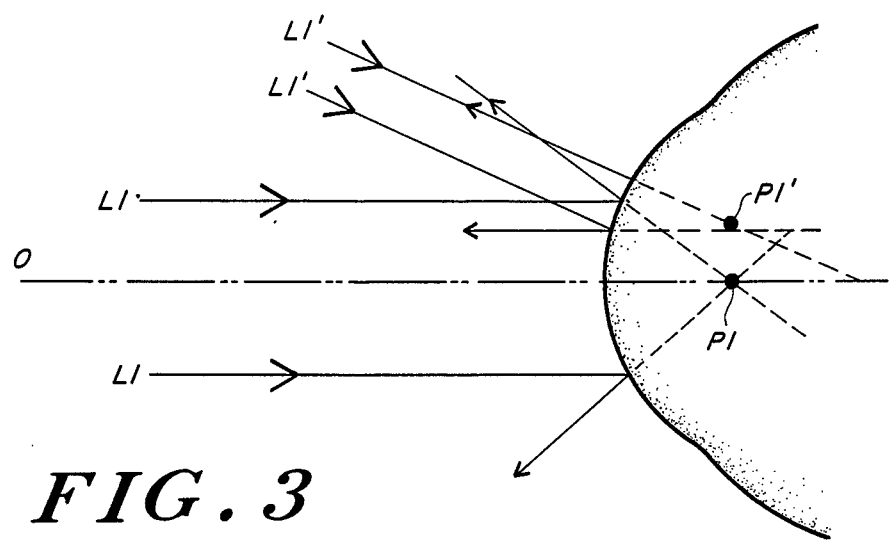
FIGS. 3, 4 show the position of Purkinje images as a function of incident beam illumination angle.

FIG. 3 shows the effect upon the location of the first Purkinje image P1 of moving the incident light from a first position having rays L1 directed parallel to the optical axis to a second position with rays L' directed downwardly toward the axis. The above axis illumination, corresponding to the orientation of the light source shown in FIG. 1A, displaces the image of P1 to a position P1' above the central axis of the eye.

Figure 4:
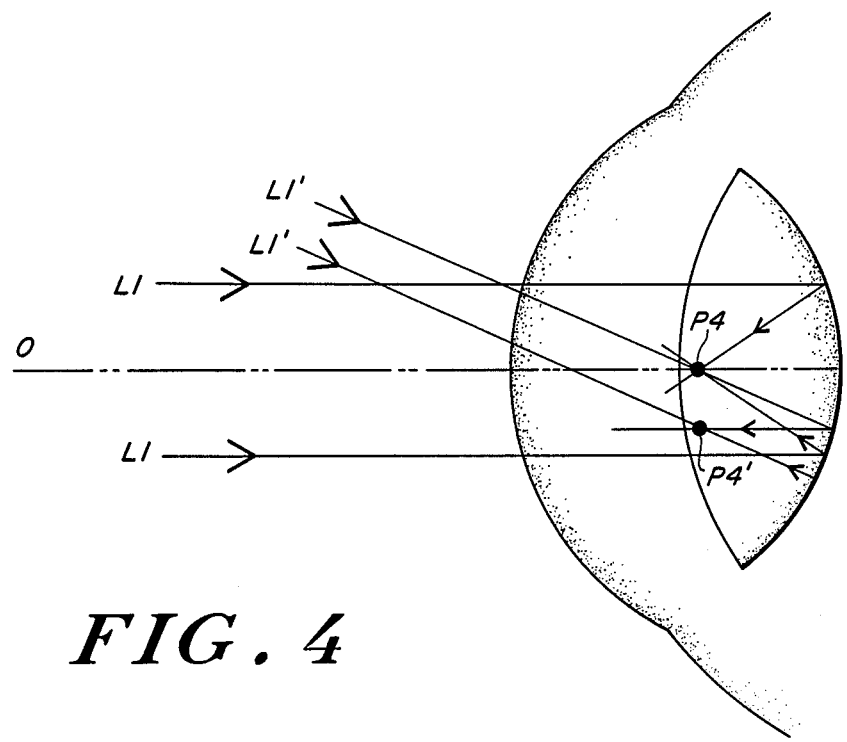

FIG. 4 shows the corresponding displacement caused by above-axis illumination L' on the fourth Purkinje image. As shown, the fourth image (P4) is displaced from the axis to a new position P4' below the axis.

Returning now to FIG. 2, it will be seen that frame 34 holds light 9 so as to direct a collimated beam at the cornea from above. The effect of so illuminating the eye with a beam of incident light directed at the cornea from above the optical axis, is to cause the two nearly collinear Purkinje images P1 and P4 to become spaced apart above and below the axis respectively. When the illumination lies directly in the vertical plane passing through the optical axis, the two Purkinje images lie directly above and below the optical axis. However, when the beam is angularly displaced from that plane, each of the Purkinje images is offset to a different side of the axis, due to their optical properties noted above.

The foregoing remarks apply with corresponding modifications, to the position assumed by the Purkinje images when illuminated from a side. In particular, when the direction of lateral illumination is in a horizontal plane containing the optical axis, as illustrated in FIG. 1B, the Purkinje images lie along a horizontal line. When the incident illumination is at an angle to the horizontal plane, the images lie along a skew line.

Figure 5A:
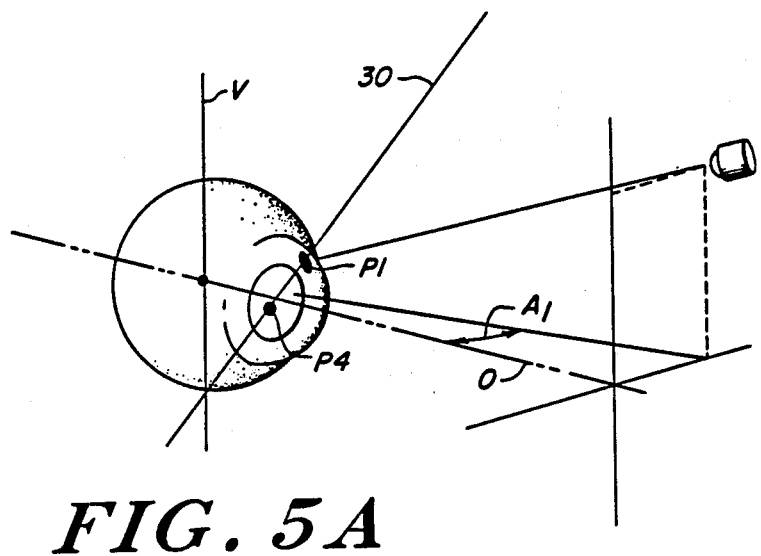
FIGS. 5A and 5B show, respectively, a schematic representation of the embodiment of FIG. 2 in a first orientation in relation to the optical axis and the view in that orientation of the Purkinje images.
Figure 5B:
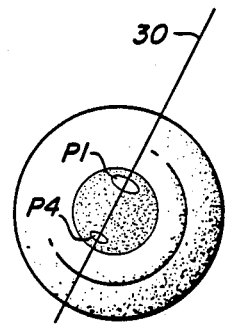

FIG. 5A is a schematic perspective view of the eye in relation to the light in a test plane according to the present invention rotatable about a vertical axis, and offset from the optical axis by a horizontal angle. As shown, a vertical test plane containing both the light source 9 and a the central vertical axis V of the eye is displaced at angle A1 about the central vertical axis with respect to the optical axis 0. When illuminated in this position, the first Purkinje image P1 is displaced toward the light source 9 and the fourth Purkinje image P4 is displaced away from the plane of the light source. The two images thus determine a line 30 which is skew with respect to the central vertical axis V. FIG. 5b shows the image of the eye as it appears on monitor 27 when the test plane 31 offset from the optical axis (0) as in FIG. 5A.

Figure 6A:
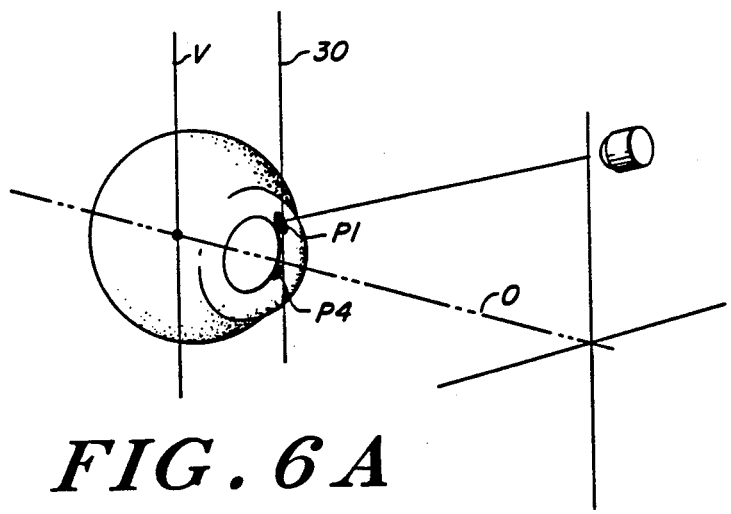
FIGS. 6A and 6B show, respectively, the invention in a second orientation aligned with the optical axis and the view in that orientation of the Purkinje images.
Figure 6B:
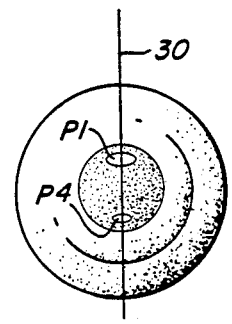

FIG. 6A is a schematic perspective view corresponding to FIG. 5A of the eye in relation to the test plane 31 when frame 19 has been rotated about vertical axis V so that the light source 9 is aligned in the same vertical plane as the optical axis. In this case, i.e., when there is no horizontal component of rotation of the eyeball with respect to the plane of the light source, both the first and fourth Purkinje images lie on a vertical line 30, parallel to the central vertical axis (V) of the eye. FIG. 6B shows a view as seen on the monitor of the eyeball and the Purkinje images in this case. It will be seen that the vertical alignment of line 30 determined by the Purkinje images may be visually ascertained by a clinician, with no special measuring instrumentation.

The apparatus and method of the invention permits the clinician to determine when the light source is aligned in a vertical plane with the optical axis by simply inspecting the alignment of the Purkinje images. Since the light may easily be aligned initially with the external target 16, the measure of angular rotation as determined from the graduated scale 26 between the initial alignment of frame 19 with target 16, and the alignment when the two images form a vertical line (30, FIG. 6B) gives a direct angular measurement of the amount by which the visual axis of the eye differs from the optical axis of the eye.

When the instrument of the present invention is aligned so that the light is aimed at the eye from the side, and is pivoted up and down about the horizontal axis (H) of the eye, then the displayed Purkinje images are offset on either side of the optical axis and determine a horizontal line when the light sources is aligned in the same plane as the optical axis. Using this property, the vertical component of angular orientation of the optical axis, or the vertical squint angle may each be directly determined.

Returning now to FIG. 2, it will be seen that frame 19 comprises adjustable frame clamp members 32 having vertical side rods 33, and horizontal rods 34 upon which clamps holding the light source and the camera may be adjustably mounted. This structure permits the light and camera to be aimed at the eye in either a horizontal or a vertical plane. Bars 33, 34 also permit the dimensions of frame 32 to be varied, so as to vary the angle of illumination or imaging of the eye. Furthermore, frame 19 comprises, in addition to a pivot structure about axis 21, a second pivot structure 35 about a horizontal axis 36 which, by motion of the base 18 and vertical adjustment of the frame may be brought into alignment with the horizontal axis (M of FIG. 1B) of a subject's eye. Thus, the single instrument of FIG. 2 can display Purkinje images while illuminating the eye with a light source either horizontally rotated about the axis V, or vertically rotated about the axis H of the eye.

The method of the invention permits examiner to determine directly the squint angles of a subject using the present invention. Illustratively, the horizontal squint angle is determined as follows. The subject is placed so that horizontal line 37 of FIG. 2 from the midpoint of the subject's eyes to the fixation target 16 is a reference line aligned with 0 degrees on scale 26. An angle medial to this line in the horizontal plane is designated positive and an angle lateral to the line is designated negative. A horizontal deviation in primary position is measured in the following way. The system is aligned with the vertical axis V of an eye coincident with pivot axis 21 of the frame, and vertical adjustment portion 25 is adjusted so the light 9 is aimed at the cornea. With this adjustment, the light beam will lie in the 0 degree vertical plane. The clinician observes the Purkinje images on the monitor and turns the frame 19 about axis 21 until the images are aligned in a vertical line while the subject is fixating on the target at 6 meters distance. This is done with both eyes. The reading on graduated scale 26 is the direction of the optical axis in each eye in the horizontal plane. If the angles are equal, the squint angle is zero. If the angles are not equal, then two cases are to be distinguished:

(1) One case arises when the angle in the fixating eye is negative. Then the numerical value of the measured angle of the non-squinting eye is added to the measured angle in the squinting eye to determine the squint angle. For example, if the measurement for the right, fixating eye is (−6) degrees and for the left eye is (−10) degrees, the squint angle is (−10+6) equals (−4) degrees. If one measures (+2) degrees in the deviated eye, the squint angle is (+2+6) equals (8) degrees.

(2) The other case arises when the angle in the fixating eye is positive; then the numerical value of the measured angle of the non-squinting eye is subtracted from the measured angle in the squinting eye to determine the squint angle. For example, if one measures (+2) degrees in the fixating eye and (−6) degrees in the deviated eye, the squint angle is (−6+(−2) equals (−8) degrees.

Another method of the invention detects existence of a non-zero squint angle. The test plane is aligned with the optical axis of one eye while the subject is fixating the target. The other (non-measured) eye is then covered, and the Purkinje images observed. Displacement of the images from the straight vertical position indicates the existence of a deviation.

Another method of the invention detects latent strabismus, or phorie. In this method, the instrument is aligned with the optical axis of an eye of a subject fixating on a target (i.e., the frame is rotated until the Purkinje images are vertical/horizontal). The eye is then covered with a cover which prevents the eye from seeing the target, but which permits the illumination and imaging of the eye by the invention. Such a cover may be, for instance, a central mask, or an infrared* filter, shown as movable filter 40 of FIG. 2. The Purkinje images are observed, and if they are non-aligned latent strabismus is indicated. By moving the light until the images are again aligned, the latent squint angle is determined.

*lignt transmittant

The illustrated prototype system utilizes a frame positioning structure from a conventional slit lamp instrument and includes pivot means for pivoting the frame around either or both of the vertical and horizontal axes of the eye. The operation of the instrument for detecting horizontal squint angle by rotation about the vertical axis of the eye has been described above. For the measurement of the vertical component of the angular orientation of an eye, the instrument is pivoted about the horizontal axis (H) of the eye. For pivoting around the horizontal axis, the light means is placed on a rod 33 directed from one side at the eye and the video camera placed on the opposite side. In that configuration, motion of the frame causing alignment of the Purkinje images in a horizontal line, parallel to the central horizontal axis of the eye indicates alignment of the light source with the optical axis of the eye in a horizontal plane. The total amount of rotation of the frame from an initial position in which the light source and target lie in the test plane, gives an objective measure of the angular position of the optical axis of the eye. The difference in the measures of the two eyes is the vertical squint angle.

The imaging of the first and fourth Purkinje images requires some care. Infrared light is preferably used for the light source, so as to provide a probe which is invisible to the subject, and which allows him to fixate on a visual target without distraction. The level of illumination actually reaching the eye in the illustrated embodiment is in the range of several hundred microwatts/square centimeter, and, owing to the low brightness of the fourth Purkinje image, requires the previously mentioned high sensitivity B&W camera for imaging.

A filter, not shown in the drawings covers the video camera lens so as to provide less sensitivity to ambient light. Tungsten illumination having substantial infrared components was found to interfere with the operation of the instrument. By fitting the camera with a broadband IR filter passing the near infrared in the range of 900–1300 nanometers, all incidential illumination from unshielded fluorescent lights in a chamber having normal levels of interior illumination was effectively blocked so that the invention could be practiced in such a chamber.

The apparatus described herein allows measurement of the angle of deviation in an amblyopic eye, and provides much greater accuracy than the corneal reflex test method. One condition in which the present invention could not be used is in the presence of a cataract, which would preclude formation of the fourth Purkinje image. The invention is otherwise of quite general use.

It will be appreciated that the invention has been described in relation to particular embodiments, and with respect to several particular methods of practice. The invention having been thus described, other variations and modifications will occur to those skilled in the art, and all such further embodiments are included within the scope of the following claims.

What is claimed is:

1. A method of determining the angular orientation of an eye of a subject fixating on a target, such method comprising the steps of:
   A. illuminating an eye of the subject with a collimated beam of a light source mounted on a pivotal frame constrained for rotational motion about a frame axis said frame being aligned so that so that the frame axis is coincident with a selected central axis of the eye, said light source directing light at the subject's eye at an illumination angle offset from the eye's optic axis so that the first and fourth Purkinje images of said light reflected from said eye are distinctly separate and form a visually determinable line when viewed from a direction offset from the optic axis by said illumination angle on a side thereof opposite to the light source;
   B. viewing from said direction offset from the optic axis, the first and fourth Purkinje images of the light reflected from the eye of the subject; and
   C. rotating the frame about the central axis while illuminating the eye and viewing the Purkinje images until the first and fourth Purkinje images determine a line parallel to the central axis, whereby the optical axis of the eye is determined to lie in a plane defined by the central axis and the light source, whereby said angular orientation of the frame provides a direct measure of the orientation of said optic axis.

2. A method according to claim 1, for the detection of latent strabismus, comprising the further steps of:
   D. covering the eye with a cover blocking the visual field of the eye but not blocking the illuminating and viewing of the eye; and
   E. observing whether the first and fourth Purkinje images continue to determine a line parallel to the central axis, and deterimining latent strabismus to be present in the eye if the images then determine a line not parallel to the central axis.

3. A method according to claim 1, further including the steps of
   (i) initially aligning the frame such that the light source is coplanar with said central axis and the target, and
   (ii) after step C, measuring the change in angular orientation of the light source about the central axis thereby determining the angle between the visual axis and the optical axis of the subject's eye.

4. A method of determining the angular orientation of an eye of a subject fixating on a target, such method comprising the steps of:
   A. illuminating an eye of the subject with a collimated beam of a light source constrained for rotational motion about an axis coincident with a selected central axis of the eye;
   B. viewing first and fourth Purkinje images of the light in the eye of the subject;
   C. rotating the light source about the central axis while illuminating and viewing until the first and fourth Purkinje images determine a line parallel to the central axis, whereby the optical axis of the eye is determined to lie in a plane defined by the central axis and the light source; then
   D. covering the eye with a cover blocking the visual field of the eye but not blocking the illuminating and viewing of the eye;
   E. rotating the light source about the central axis while illuminating and viewing until the first and fourth Purkinje images determine a line parallel to the central axis; and
   F. taking as the measure of latent squint angle the difference between the angular orientation of the light source about the central axis after C and the angular orientation after step E.

5. A clinical apparatus for determining the angular orientation of a subject's eye, such apparatus having a stand with a headrest for supporting the head of a subject in a defined position, and further comprising
   light means for directing light at the subject's eye,
   pivotal frame means supporting said light means for pivoting about a horizontal or a vertical test axis,
   alignment means for aligning said pivotal frame means with respect to the stand so that the test axis coincides with a central axis of the eye of the subject,
   angle display means for indicating the angular position of said pivotal frame means as it pivots,
   said light means being supported by said frame means so as to direct light to the subject's eye at an illumination angle offset from the eye's optic axis so that the first and fourth Purkinje images of said light reflected from said eye are distinctly separate when viewed from a direction offset from the optic axis by said illumination angle on a side thereof opposite to the light means, and
   observation means on said frame means for observing the first and fourth Purkinje images from said direction offset by said illumination angle,
   whereby the angle display means displays the angular orientation of the optical axis of the subject's eye upon the pivoting of said pivotal frame means to locate the observed Purkinje images along said test axis.

6. Apparatus according to claim 5 wherein the light means comprises an infrared light source.

7. Apparatus according to claim 5 wherein the observation means comprises a video camera.

8. Apparatus according to claim 5, further comprising adjustment means for varying the illumination angle so as to adjust the spacing of the first and fourth Purkinje images formed by the light in eyes of subjects that have differing dimensions.

9. Apparatus according to claim 5, further comprising cover means for selectively blocking the subject's eye from viewing a front visual field while not blocking illumination and observation of the eye by said light means and said observation means.

10. Apparatus according to claim 9, wherein the cover means comprises an infrared transmission filter.

11. Apparatus according to claim 5, wherein said pivotal frame comprises first pivot means for pivoting about a horizontal axis and second pivot means for pivoting about a vertical axis.

12. A clinical apparatus for determining the angular orientation of a subject's eye, of the type for use with a stand and a headrest for supporting the head of a subject in a defined position, and further comprising
   light means for directing light at the subject's eye,
   pivotal frame means supporting said light means for pivoting about at least one of a horizontal or a vertical test axis,
   alignment means for aligning said pivotal frame means with respect to the stand so that the test axis coincides with a central axis of the eye of the subject, angle display means for indicating the angular position of said pivotal frame means as it pivots, said light means being supported by said frame means so as to direct light to the subject's eye at an illumination angle offset from the eye's optic axis so that the first and fourth Purkinje images of said light reflected from said eye are distinctly separate and form a visually determinable line when viewed from a direction offset from the optic axis by said illumination angle on a side thereof opposite to the light means, whereby by observing the first and fourth Purkinje images from said direction offset by said illumination angle, and pivoting said pivotal frame means to locate the observed Purkinje images along said test axis, the angle display means displays the angular orientation of the optical axis of the subject's eye.

13. Apparatus according to claim 12, wherein the light means comprises an infrared light source.

14. Apparatus according to claim 12, further comprising a video camera coupled to said frame means for imaging said first and fourth Purkinje images from said direction offset from the optic axis.

* * * * *

UNITED STATES PATENT AND TRADEMARK OFFICE
CERTIFICATE OF CORRECTION

PATENT NO. : 4,729,652

DATED : Mar 8, 1988

INVENTOR(S) : Rolf Effert

It is certified that error appears in the above-identified patent and that said Letters Patent is hereby corrected as shown below:

Column 6, line 19, replace "and a the central vertical axis" with --and the central vertical axis--.

Column 6, line 61, replace "light sources is aligned" with --light source is aligned--.

Column 10, line 5, replace "central axis after C" with --central axis after step C--.

Signed and Sealed this

Twenty-fourth Day of April, 1990

Attest:

HARRY F. MANBECK, JR.

*Attesting Officer*     *Commissioner of Patents and Trademarks*